(12) United States Patent
Silderhuis

(10) Patent No.: US 8,198,598 B2
(45) Date of Patent: Jun. 12, 2012

(54) STERILIZATION DEVICE AND LAMP HOLDER THEREFOR

(75) Inventor: Hermannus Gerhardus Maria Silderhuis, Enschede (NL)

(73) Assignee: Virobuster Intellectual Property B.V., Rotterdam (NL)

(*) Notice: Subject to any disclaimer, the term of this patent is extended or adjusted under 35 U.S.C. 154(b) by 153 days.

(21) Appl. No.: 12/602,389

(22) PCT Filed: Jun. 2, 2008

(86) PCT No.: PCT/NL2008/050335
§ 371 (c)(1),
(2), (4) Date: Aug. 27, 2010

(87) PCT Pub. No.: WO2008/147198
PCT Pub. Date: Dec. 4, 2008

(65) Prior Publication Data
US 2010/0308232 A1 Dec. 9, 2010

(30) Foreign Application Priority Data
Jun. 1, 2007 (NL) .................................... 2000676

(51) Int. Cl.
*G01J 1/42* (2006.01)
(52) U.S. Cl. ..................................... 250/373
(58) Field of Classification Search .................. 250/372
See application file for complete search history.

(56) References Cited

U.S. PATENT DOCUMENTS

| | | | |
|---|---|---|---|
| 5,612,001 A * | 3/1997 | Matschke | ..................... 96/224 |
| 5,742,063 A | 4/1998 | Scroggins et al. | |
| 6,022,511 A | 2/2000 | Matschke | |
| 6,984,834 B2 | 1/2006 | Alexander et al. | |
| 2004/0061069 A1 | 4/2004 | Schalble et al. | |
| 2004/0211926 A1 | 10/2004 | Alexander et al. | |
| 2005/0238531 A1 | 10/2005 | Trifu et al. | |
| 2006/0000360 A1* | 1/2006 | Shou et al. | ..................... 96/224 |
| 2006/0151369 A1* | 7/2006 | Hegmegi | ..................... 210/149 |
| 2006/0177356 A1* | 8/2006 | Miller | ..................... 422/121 |
| 2008/0019861 A1 | 1/2008 | Silderhuis | |
| 2008/0112844 A1 | 5/2008 | Garrett | |

FOREIGN PATENT DOCUMENTS

WO 01/55037 A 8/2001
WO 2005/039659 A 5/2005

* cited by examiner

Primary Examiner — David Porta
Assistant Examiner — Marcus Taningco
(74) Attorney, Agent, or Firm — Abel Law Group, LLP (57) ABSTRACT

A device for subjecting air to UV(C) radiation comprises a UV(C) treatment chamber comprising a UV(C) source, a measuring device comprising one or more of a temperature sensor which measures the temperature on the wall of the UV(C) source; two temperature sensors downstream and upstream of the UV(C) source; and a UV(C) sensor for determining the intensity of the UV(C) radiation. The UV(C) source comprises at least one UV(C) lamp which is held by a lamp holder. The lamp holder comprises positioning elements for holding the measuring device and the lamp(s) in a fixed position. Electrical supply wires and signal wires are arranged such that they are shielded from the radiation from the UV(C) lamp(s).

12 Claims, 6 Drawing Sheets fig.1A fig.1B fig.2 fig. 3 fig. 5 fig. 4 fig.6

STERILIZATION DEVICE AND LAMP HOLDER THEREFOR

BACKGROUND OF THE INVENTION

1. Field of the Invention

The invention relates to a device for subjecting air to UV(C) radiation, which device comprises:

a housing with an air inlet and an air outlet;

a UV(C) treatment chamber which is present in the housing and in which is accommodated a UV(C) source which subjects the passing air to a UV(C) treatment, the effectiveness of which depends on the intensity of the UV(C) radiation and on the residence time of the air in the UV(C) treatment chamber;

measuring means for measuring the value of at least one parameter representative of this intensity and for generating a measurement signal corresponding with this value to an external processor, in which a process window is stored which indicates the limits of the process effectiveness and the corresponding limits of the intensity and the residence time;

which measuring means comprise at least one of the following measuring units:

(a) a temperature sensor which measures the temperature on the wall of the UV(C) source;

(b) two temperature sensors which are placed respectively downstream and upstream relative to the UV(C) source in order to determine the heating of the passing air caused by the UV(C) source;

(c) a UV(C) sensor for determining the intensity of the UV(C) radiation at a selected position in the UV(C) treatment chamber;

which UV(C) source comprises at least one UV(C) lamp which is held by a lamp holder, which comprises terminal openings into which electrical terminal pins protruding from the or each UV(C) lamp can be inserted, which terminal openings are connected to electrical supply wires with respective insulating sheaths, which electrical supply wires can be connected with their free ends to an electric power supply unit; and which measuring means are connected to electric signal wires with respective insulating sheaths, which electrical signal wires can be connected with their free ends to the external processor.

Such a device is known from international patent application WO-A-2005/039659 of applicant.

2. Discussion of Background Information

It is known that many physical, biological and biophysical processes are subjected to influencing factors which can often be expressed in terms of change in the values of relevant process parameters. To enable such a process to be controlled in the desired manner, in particular to keep the process confined within a defined process window, it is essential that relevant parameters are measured and, on the basis thereof, these parameters and/or other related parameters are continuously adjusted in dynamic manner. In the case where the process shifts outside a process window it is thus possible to intervene on the basis of the relevant measurement data, so that the process can be brought once again within the process window on the basis of new settings of one or more parameters.

As the process window becomes narrower, i.e. is determined within values that are closer together, the more accurate the measurements must be.

In the present case of a device intended for sterilization of air there are physical and biophysical processes which have a common factor, i.e. the time, expressed in seconds, and a related flow rate of the air flowing through the device. In order to be able to control such a process in the desired manner a reliable measurement of, among other quantities, the flow rate of the throughflow air is therefore necessary. A flow rate measurement can be performed by determining the (average) air speed at a given throughflow area.

Diverse methods exist for measuring air speed. Several examples thereof are described briefly hereinbelow.

(A) A so-called vane-anemometer comprises a propeller with precisely known aerodynamic properties which is driven by throughflow air. The propeller is placed in the airflow and, for instance by making use of an optical sensor, the rotation speed of the propeller is measured. The frequency of the propeller or the rotation speed is converted via a calibration table into an electrical signal which is representative of the air speed.

(B) A hot-wire anemometer makes use of a wire of resistance material through which an electric current is passed. The wire is heated by the electric current running therethrough and obtains an initial surface temperature at an air flow rate with the value zero. When air then begins to flow therealong, a heat transfer will take place between the wire and the passing air. As a result the wire will cool, which is expressed in a changing resistance value. An electrical measuring and control circuit then transmits a stronger current through the wire, until the initial temperature has once more been reached. The increase in the current or in the power fed to the wire in the dynamic situation relative to the static situation can then be converted to a value of the air speed.

(C) Manometers can also determine the air speed on the basis of a pressure difference between two measuring points.

(D) A further possibility is the use of venturi means.

SUMMARY OF THE INVENTION

It is an object of the invention to embody the known device such that, under the most diverse dynamic conditions, the momentary parameter values will always be such that the process will remain within a process window which is, if desired, very narrow.

It is a further object of the invention to ensure that the device consists of few components so that the device is suitable for a very rapid and simple maintenance procedure and for carrying out repairs, particularly at the end of the useful life of components subject to wear and ageing. It is a further object of the invention to embody the device such that it functions very reliably under any conceivable conditions and, after replacement of determined components, in particular the UV(C) lamp or lamps, further functions correctly within the selected process window automatically and without the necessity for any regulation or adjustment.

It is a further object of the invention to embody the device of the described type such that the generally weak measurement signals are not disrupted by the electrical and/or the magnetic field generated by the alternating current running through the supply wires for the lamp or lamps, in general a current with the mains frequency of 50 or 60 Hz.

It is yet another object of the invention to embody the device of the described type such that the insulating sheaths of the electrical supply wires and of the signal wires are not subject to premature ageing and degradation resulting from the action of UV(C) radiation.

With a view to the above stated objectives, the invention provides a device of the type stated in the preamble for sterilizing air flowing through the device, which device has the feature according to the invention that the lamp holder comprises positioning means for positioning the lamp(s) in a fixed, defined position;

the lamp holder holds the measuring means at a fixed position; and the electrical supply wires and the signal wires are located such that they are shielded from the radiation from the UV(C) lamp(s).

The or each lamp is fixed by the positioning means without any degree of freedom relative to the lamp holder. No lamp can therefore perform either a translation or a rotation in any direction. Such a blocking of all six degrees of freedom requires a fixation at three points. Per se known and commercially available PL-L-lamps, which are suitable for the device according to the invention, for instance comprise two electrical terminal pins inserted in a manner to be further described below into the corresponding terminal openings of a lamp base which is rigidly connected to the lamp holder. The lamp is fixed at a distance from the lamp base, for instance by means of a resilient clamp at the free end zone. In this way the lamp is fixed releasably in a fixed position relative to the lamp holder. This is important for preventing malfunctions resulting from an electrical contact which is not fully controlled when the lamp is askew and for ensuring that the UV(C) radiation in the UV(C) treatment chamber always meets predetermined criteria, in particular the homogeneity of the radiation.

The treatment chamber will generally be provided with a mirrored wall. The effective reflection in this wall depends partly on the position of the lamp relative to this wall. Owing to the well-defined positioning of the lamp or the lamps, the intensity of the UV(C) radiation in the UV(C) chamber is very predictable and reproducible, also in the case that a lamp is replaced.

It is of further importance that the measuring means are held in a fixed position. One fixed measuring point must for instance be chosen for the purpose of measuring the intensity of the UV(C) radiation in the UV(C) treatment chamber so that, for instance after a lamp has been changed, the intensity of the UV(C) radiation in the UV(C) treatment chamber can once again be measured under exactly the same conditions.

The prevention of electrical interference between the supply wires and the signal wires can take place by laying these different types of wire at a sufficiently great mutual distance and by shielding thereof with an electrical and/or a magnetic shield.

As discussed above, the device according to the invention can advantageously have the special feature that the supply wires and the signal wires are located relative to each other such that the electrical supply current induces practically no electrical interference signal in the signal wires.

In a specific embodiment the device has the special feature that the lamp holder, the positioning means and the measuring means are assembled into an integrated unit. In the case of desired maintenance or possibly necessary repair or replacement of a component, such an integrated unit can be easily removed as one whole in a very short time, can optionally be treated or provided with a new component, or replaced with a replacement unit.

The invention further relates to a lamp holder adapted to serve as component for a device according to any of the foregoing claims, which lamp holder forms an integrated unit together with positioning means for at least one UV(C) lamp and measuring means.

Using the invention the performance level that is sought can be realized in relatively simple manner, i.e. for controlling parameters relevant to the process such that, under the most diverse and varying conditions, it is ensured that the device renders harmless at least a chosen fraction of the incoming population of harmful micro-organisms, for instance bacteria and viruses. A remaining relative population of a maximum of $10^{-4}$ can for instance be envisaged. Considerably lower values can also be realized with the device according to the invention.

The device according to the invention is able to maintain this high degree of sterilization for a very long time, i.e. essentially for the whole lifespan of the UV(C) lamps.

According to the invention the control of the process can be combined with a measurement. The following considerations may for instance be applicable here.

(A) A series inductor or another power unit supplies power for power supply to the lamp or lamps.

(B) On the basis of the supplied electrical energy each lamp generates UV(C) radiation with which micro-organisms present in the passing air are rendered harmless.

(C) During the operation of the device each lamp heats the passing air.

(D) A temperature measurement for the purpose of determining the change in the surface temperature of the lamp, from a situation with air speed zero to the situation with a value of the air speed differing from zero, can be converted into a value of the air speed or of the air flow rate.

The combination of A and B describes a physical and a biophysical process. The combination of C and D in fact describes a measurement in accordance with the hot-wire anemometer as discussed above. Use is thus made of the fact that the lamp, which is intended to generate UV(C) radiation for the purpose of rendering harmless harmful micro-organisms, also heats the air and can thus serve not only as process component but also as measuring component.

The mechanical shielding of the wires not only has the effect that the insulation is protected against degradation resulting from the action of UV(C) radiation, but is also a screening against the direct radiant heat from the lamp.

Fixed positioning of each lamp and fixing thereof in this position ensures that no movement whatsoever of the lamp is possible during transport and during operation of the device. The safety requirements set in this respect (UL, CE, KEMA) are here also met. According to these requirements, a minimum clamping force is necessary between the electrical terminal pins of each lamp and the electrical terminal openings in the lamp base in order to prevent local sparking.

As will be discussed hereinbelow in more detail with reference to the figures, tubular passages of the wires can also have the function of fixing elements with which the lamp holder is attached to the housing of the device.

BRIEF DESCRIPTION OF THE DRAWINGS

The invention will now be elucidated with reference to the accompanying drawings. In the drawings.

DETAILED DESCRIPTION OF THE INVENTION

The device drawn in the figures is an integrated unit and comprises a lamp holder 17 to be described in more detail hereinbelow, with a frame which is a monolithic unit and is for instance embodied in corrosion-protected steel or other suitable type of metal, and comprises measuring means to be described below.

Figure 1A:
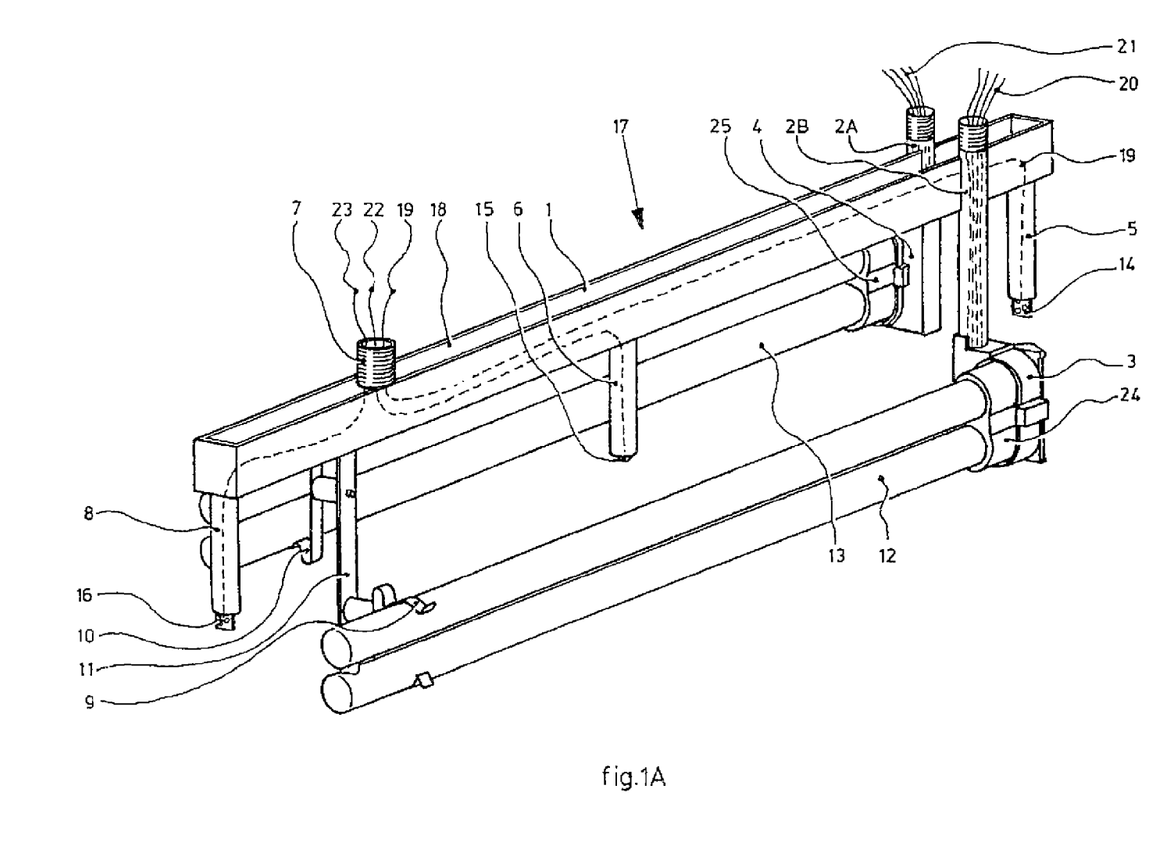
FIG. 1A shows a perspective view of an integrated unit comprising a lamp holder, positioning means and measuring means, which lamp holder also holds two UV(C) lamps.
Figure 1B:
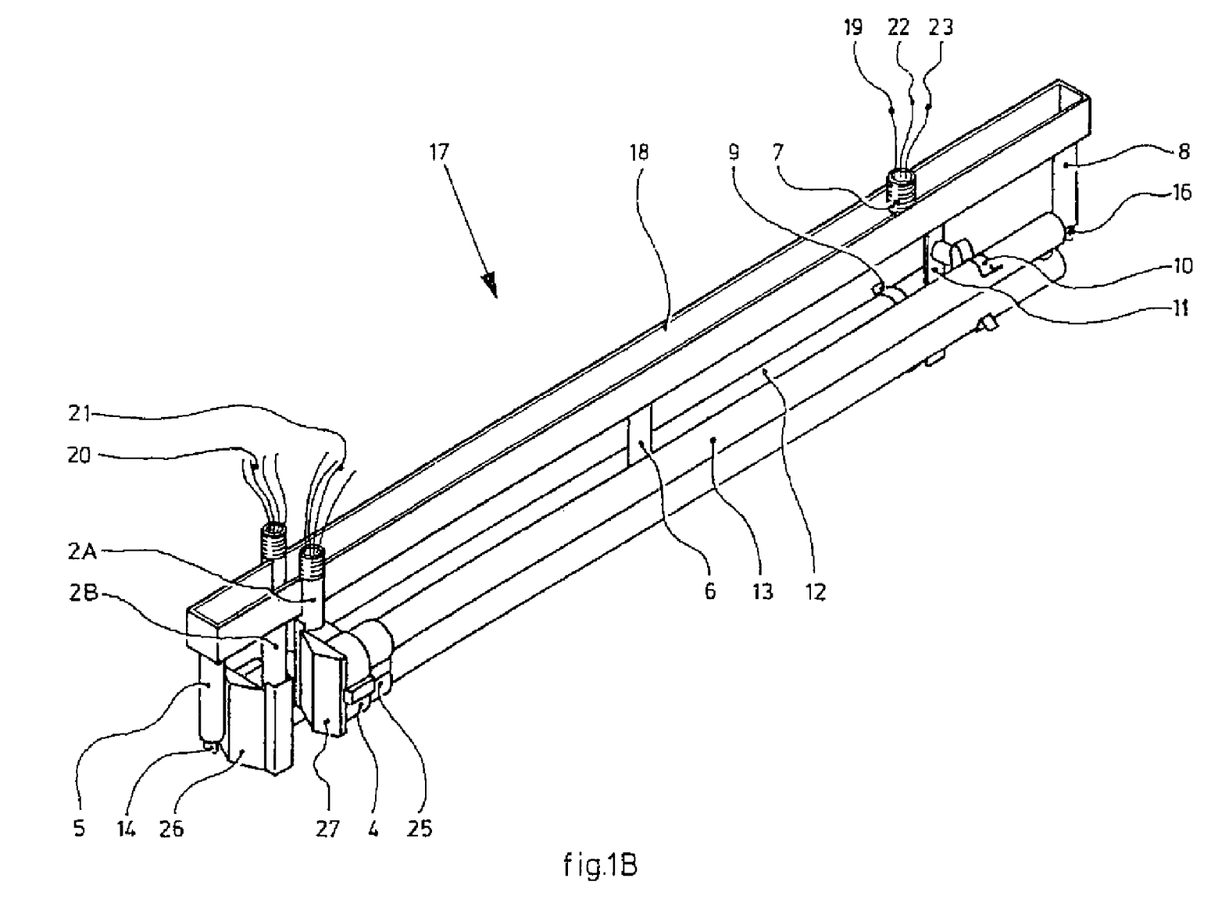
FIG. 1B shows a perspective view from the other side.

Frame 1 comprises an elongate, generally U-shaped profile 18 which is open on the top side as seen in FIG. 1 and which holds the following tube stubs;

a tube stub 5, at the end of which a temperature sensor 14 is accommodated. Via a through-hole in profile 18 tube stub 5 connects to the interior of this profile for passage of a signal line 19 which is connected to sensor 14 for measuring the temperature T1 of the incoming air.

two carriers 2A and 2B embodied as tube stubs and carrying lamp base holders 3 and 4 respectively. In each of the tube stubs 2A and 2B are accommodated four wires which are designated respectively 21 and 22. As shown clearly in FIG. 1, wires 21 and 22 extend only through tube stubs 2A and 2B and not through profile 18. This is important in respect of preventing electrical and magnetic interference between supply wires 20, 21 and the signal wires, of which line 19 has already been described.

a carrier 6 embodied as tube stump and carrying a UV(C) sensor 15 on its free underside. A signal line 22 is connected to the UV(C) sensor. This wire 22 is guided outside via profile 18.

a carrier 8, of the same type as carrier 5, which carries on its free underside a temperature sensor 16 for measuring the temperature T2 of the outgoing airflow. Connected to sensor 16 is a signal line 23 which is guided outside via profile 18.

Welded fixedly to the profile is a tube stub 7 through which signal lines 19, 22, 23 extend in order to be carried outside, so that they can generate their signals to a processor.

Carriers 2A and 2B and tube stub 7 are all three provided with external screw thread. The wall of the UV(C) treatment chamber (not drawn) has three holes arranged at corresponding positions. Carriers 2A and 2B and tube stub 7 can be inserted therethrough and then be secured by means of nuts. The position of elongate lamps 12, 13 in the UV(C) treatment chamber is hereby completely fixed.

Lamps 12, 13 are inserted with their respective lamp bases 24, 25 into the respective lamp base holders 3, 4. As generally known and usual, and therefore not drawn, each of the lamps comprises four terminal pins which are inserted into respective terminal openings in the relevant lamp base holder.

Situated at the other end zone of each lamp is a lamp clamp, which lamp clamps are designated 9 and 10 respectively. Every degree of freedom of movement of each lamp is blocked with this construction.

Lamp clamps 9, 10 are held by a carrier strip 11 welded to profile 18.

In addition to being welded, said tube stubs and the carrier strips can also be connected to profile 18 by means of hard-soldering or other suitable processes.

Figure 2:
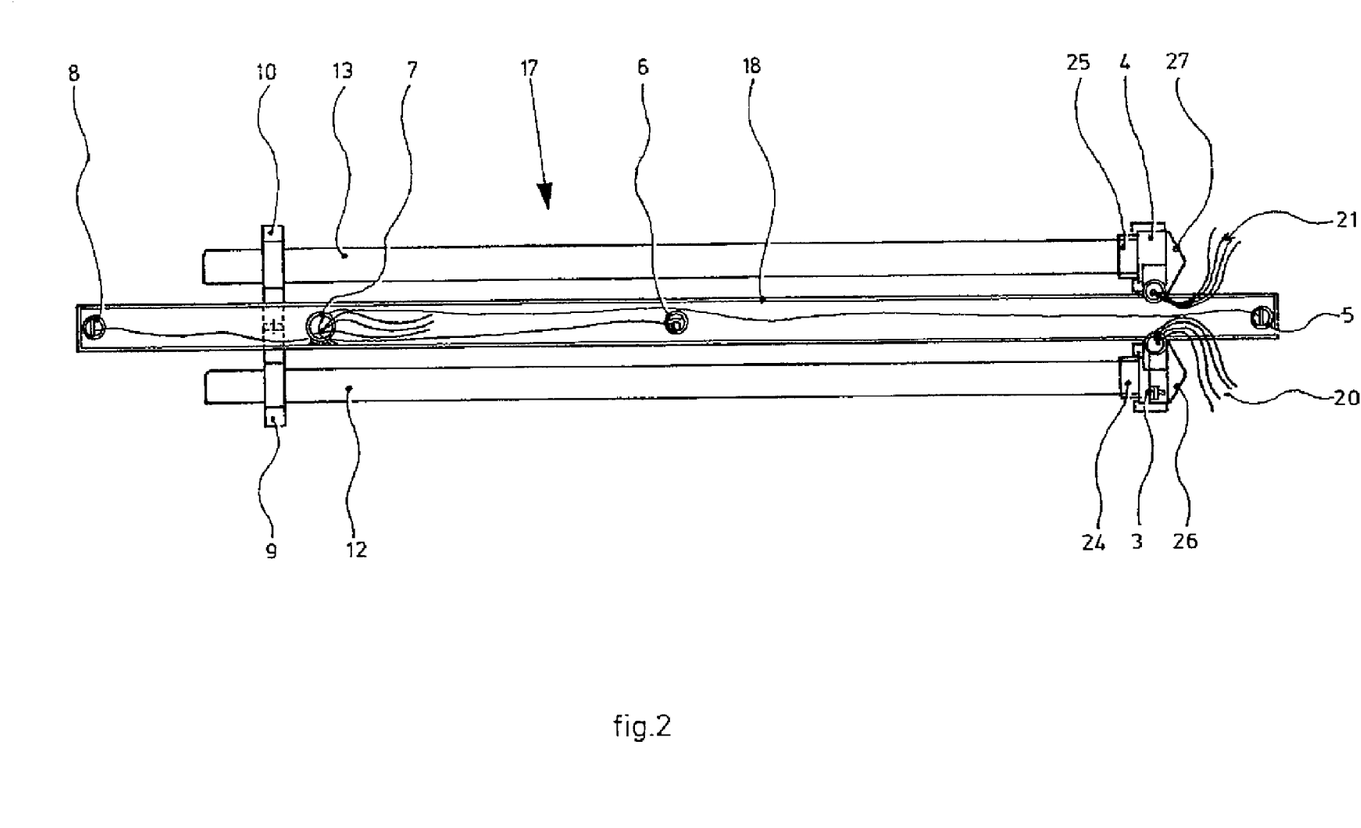
FIG. 2 shows a view from the top side of the unit according to FIG. 1.
Figure 3:
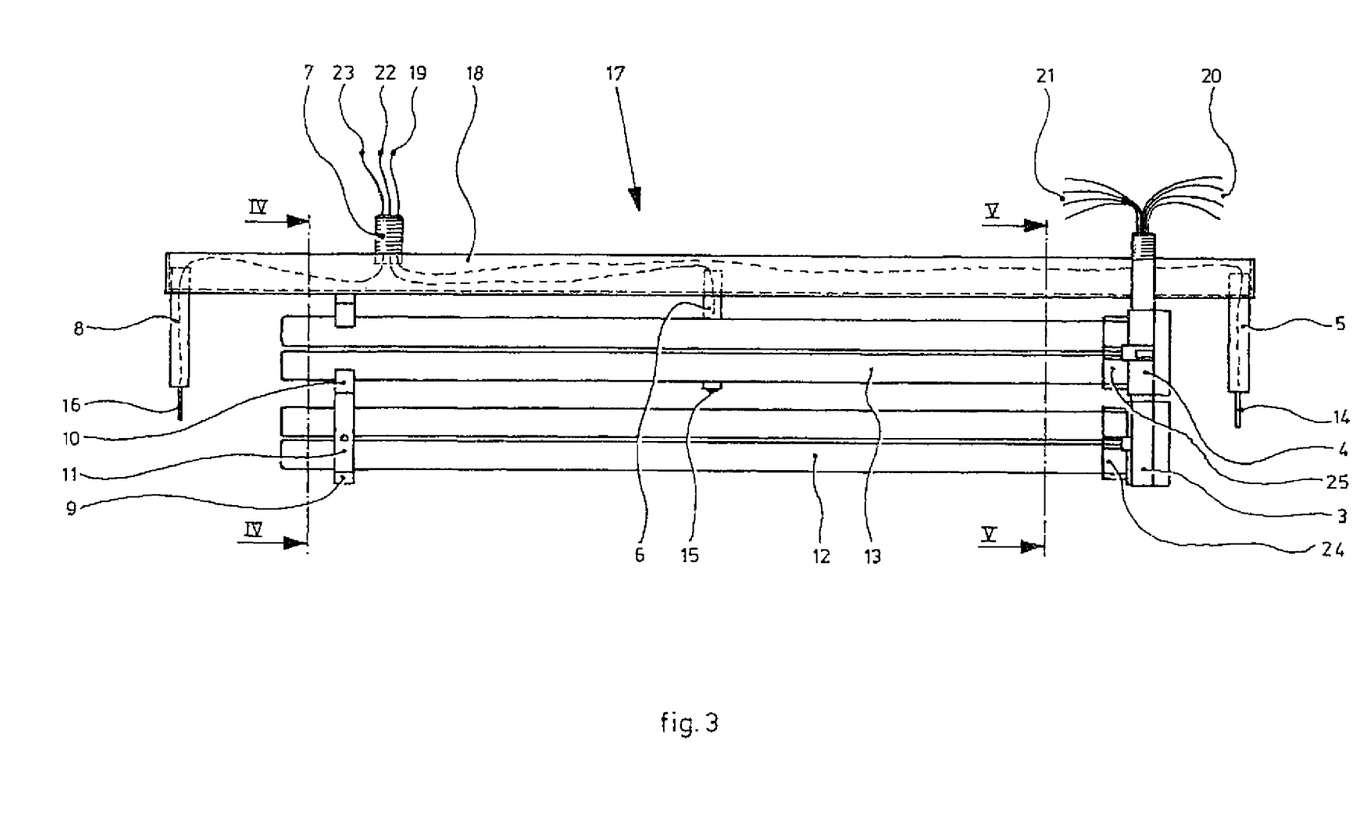
FIG. 3 shows a side view of the unit according to FIGS. 1 and 2.
Figure 4:
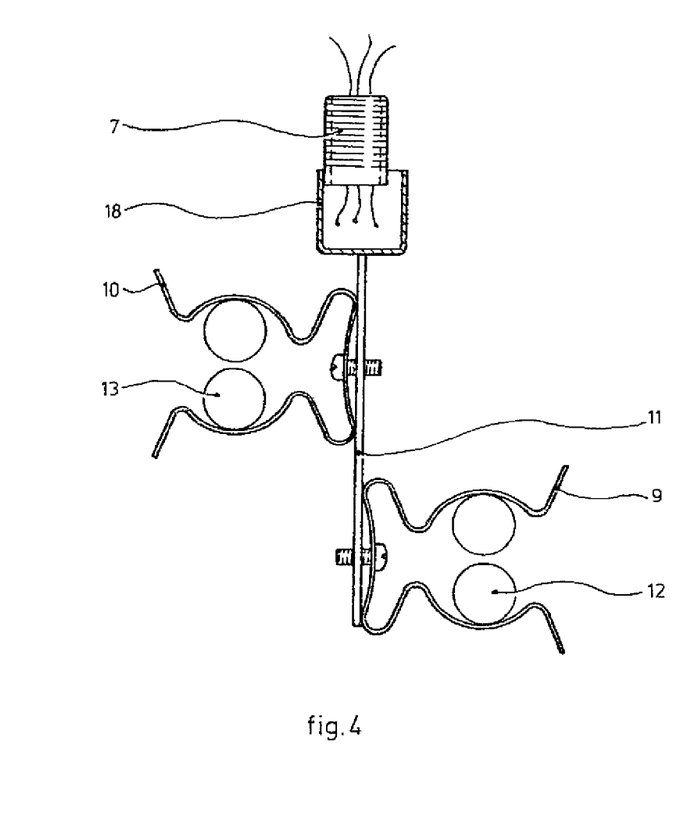
FIG. 4 shows an end view of the device according to FIGS. 1, 2 and 3.
Figure 5:
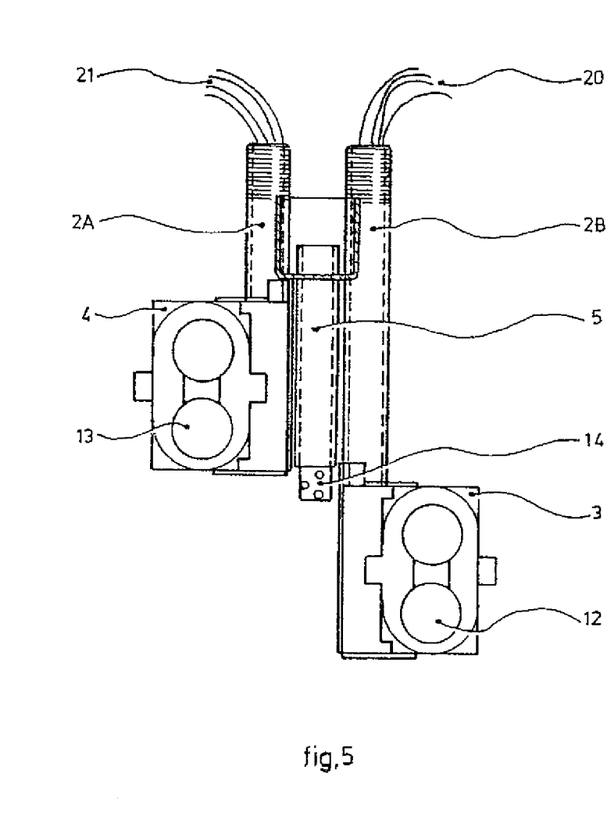
FIG. 5 shows a cross-section through the unit at the position of the lamp clamps.

Referring to FIGS. 2 and 3, attention is drawn to the fact that lamp base holders 3 and 4 are provided with streamlining elements 26 and 27 respectively placed upstream. These elements serve to cause the incoming air to flow in laminar manner along lamps 12, 13 in a smooth pattern. Streamlining elements 26, 27 can be manufactured from the same material as the other described elements of the lamp holder or frame 1.

Figure 6:
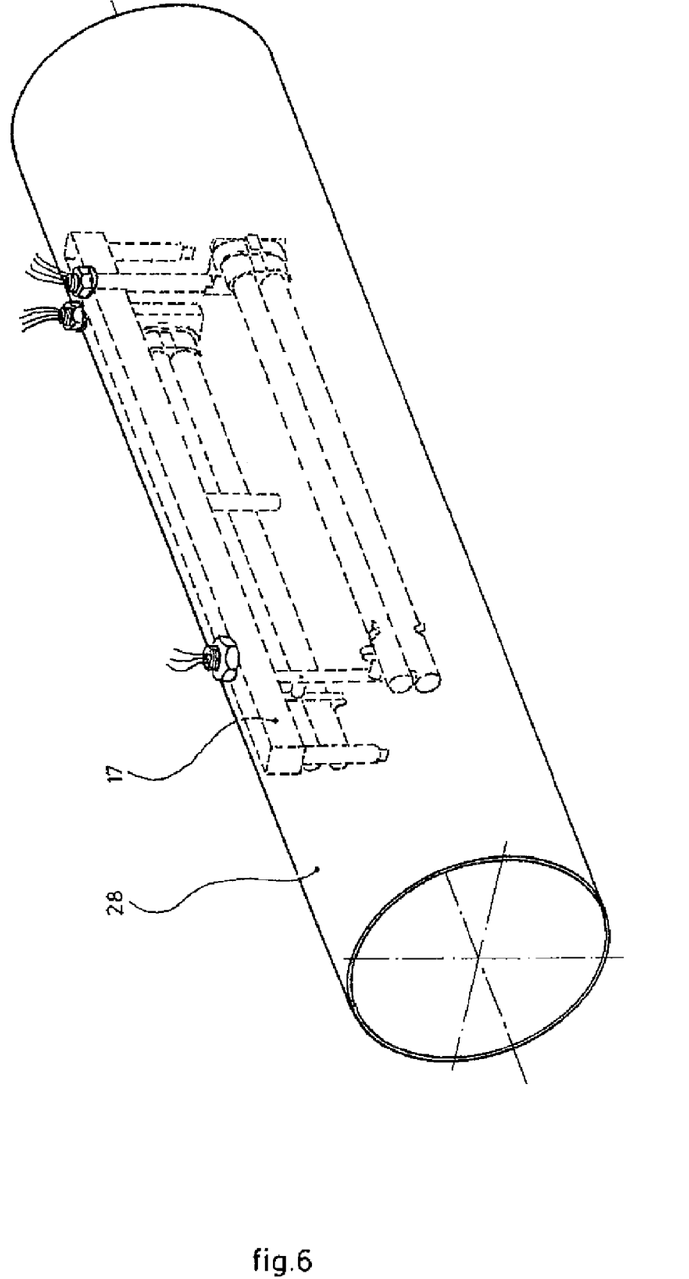
FIG. 6 shows a transparent perspective view of a UV(C) treatment chamber in which a lamp holder is positioned.

FIG. 6 shows an internally mirrored, cylindrical metal sleeve 28, which forms a UV(C) treatment chamber 28 in which lamp holder 17 is positioned. For this purpose tube stubs 2A, 2B and 7 are inserted into through-holes (not drawn) present for this purpose in sleeve 28 and secured by means of nuts.

What is claimed is:

1. A device for subjecting air to UV(C) radiation, wherein the device comprises:

a housing with an air inlet and an air outlet;

a UV(C) treatment chamber which is present in the housing and accommodates a UV(C) source which subjects passing air to a UV(C) treatment the effectiveness of which depends on an intensity of the UV(C) radiation and on a residence time of the air in the UV(C) treatment chamber;

a measuring device for measuring a value of at least one parameter which is representative of the intensity of the UV(C) radiation and for generating a measurement signal corresponding to the value of the at least one parameter to an external processor, which measuring device comprises a process window that indicates limits of process effectiveness and corresponding limits of the intensity of the UV(C) radiation and the residence time of the air in the UV(C) treatment chamber; and which measuring device further comprises at least one of:

(a) a temperature sensor which measures a temperature on a wall of the UV(C) source;

(b) two temperature sensors for determining a heating of the passing air caused by the UV(C) source which are placed respectively downstream and upstream relative to the UV(C) source; and (c) a UV(C) sensor for determining the intensity of the UV(C) radiation at a selected position in the UV(C) treatment chamber;

the UV(C) source comprising one or more UV(C) lamps which are held by a lamp holder that comprises terminal openings into which electrical terminal pins protruding from the one or more UV(C) lamps can be inserted, which terminal openings are connected to electrical supply wires with respective insulating sheaths, which electrical supply wires can be connected with their free ends to an electric power supply unit; and which measuring device is connected to electric signal wires with respective insulating sheaths, which electrical signal wires can be connected with their free ends to the external processor;

the lamp holder (i) comprising positioning elements for positioning one or more UV(C) lamps in a fixed, defined position and (ii) holding the measuring device in a fixed position; and the electrical supply wires and the signal wires being arranged to be shielded from radiation from the one or more UV(C) lamps.

2. The device of claim 1, wherein the UV(C) source comprises two UV(C) lamps.

3. The device of claim 1, wherein the measuring device comprises at least (a).

4. The device of claim 1, wherein the measuring device comprises at least (b).

5. The device of claim 1, wherein the measuring device comprises at least (c).

6. The device of claim 1, wherein the measuring device comprises at least (a) and (c).

7. The device of claim 1, wherein the measuring device comprises at least (b) and (c).

8. The device of claim 1, wherein the measuring device comprises (a), (b) and (c).

9. The device of claim 1, wherein the lamp holder, the positioning elements, and the measuring device are comprises in an integrated unit.

10. The device of claim 1, wherein the supply wires and the signal wires are located relative to each other such that substantially no electrical interference signal in the signal wires is induced by an electrical supply current.

11. An integrated unit for use in the device of claim 1, wherein the integrated unit comprises a lamp holder, positioning elements for at least one UV(C) lamp and the measuring device.

12. A method of subjecting air to UV(C) radiation, wherein the method comprises passing the air through the device of claim 1.

* * * * *